US007547543B2

(12) United States Patent
Staels et al.

(10) Patent No.: US 7,547,543 B2
(45) Date of Patent: Jun. 16, 2009

(54) METHOD FOR IDENTIFYING SUBSTANCES USEFUL FOR TREATING INFLAMMATION USING THE RESPONSE ELEMENT TO THE IKBALPHA ROR RECEPTOR

(75) Inventors: Bart Staels, Petit Enghien (BE); Philippe Delerive, Levallois Perret (FR)

(73) Assignee: Genfit, Loos (FR)

( * ) Notice: Subject to any disclaimer, the term of this patent is extended or adjusted under 35 U.S.C. 154(b) by 273 days.

(21) Appl. No.: 10/344,577

(22) PCT Filed: Aug. 22, 2001

(86) PCT No.: PCT/FR01/02652

§ 371 (c)(1),
(2), (4) Date: Feb. 13, 2003

(87) PCT Pub. No.: WO02/16638

PCT Pub. Date: Feb. 28, 2002

(65) Prior Publication Data
US 2005/0260575 A1    Nov. 24, 2005

(30) Foreign Application Priority Data
Aug. 23, 2000   (FR) .................................. 00 10857

(51) Int. Cl.
*C12N 15/00* (2006.01)
*C12N 15/63* (2006.01)
*C12Q 1/00* (2006.01)
*C12Q 1/66* (2006.01)
*C12Q 1/68* (2006.01)
*C12N 15/67* (2006.01)
*C12N 15/11* (2006.01)

(52) U.S. Cl. ................... 435/320.1; 435/69.1; 435/325; 435/6; 435/7.21; 435/8; 536/24.2

(58) Field of Classification Search ............... 435/6, 435/7.1, 320.1, 69.1
See application file for complete search history.

(56) References Cited

U.S. PATENT DOCUMENTS

| 5,747,661 | A |  | 5/1998 | Mangelsdorf et al. |
| 5,846,714 | A |  | 12/1998 | Baldwin et al. |
| 5,939,285 | A |  | 8/1999 | Cerutti et al. |
| 5,958,683 | A |  | 9/1999 | Missbach et al. |
| 6,998,254 | B1 | * | 2/2006 | Raspe et al. ............... 435/69.1 |

FOREIGN PATENT DOCUMENTS

| EP | 0 779 361 |  | 6/1997 |
| FR | 2 776 388 |  | 9/1999 |
| WO | WO 99/17778 |  | 4/1999 |
| WO | WO 99/50660 | * | 10/1999 |
| WO | WO 99/65449 |  | 12/1999 |

OTHER PUBLICATIONS

Delerive et al, The orphan nuclear receptor RORa is a negative regulator of the inflammatory response, EMBO reports, p. 42-48 vol. 21, No. 11.*
McBroom et al, The Nonconserved Hinge Region and Distinct Amino-Terminal Domains of the RORa Orphan Nuclear Receptor Isoforms Are Required for Proper DNA Bending and RORa-DNA Interactions, Molecular and Cellular Biology, Feb. 1995, p. 796-808 vol. 15, No. 2.*
Koibuchi et al, RORa Augments Thyroid Hormone Receptor-Mediated Transcriptional Activation, Endocrinology, 1999, p. 1356-1364, vol. 140, No. 3.*
Retnakaran et al, Identification of RVR, a novel orphan nuclear receptor that acts as a negative transcriptional regulator, Molecular Endocrinology, Sep. 1994, p. 1234-1244, vol. 8.*
Harding et al, Transcriptional Activation and Repression by RORa, an Orphan Nuclear Receptor Required for Cerebellar Development, Molecular Endocrinology, 1997, p. 1737-1746, vol. 11 No. 11.*
Laflamme et al, An Essential Role of Interleukin-1b in Mediating NF-kB Activity and COX-2 Transcription in Cells of the Blood-Brain Barrier in Response to a Systemic and Localized Inflammation But Not During Endotoxemia, J of Neuro, 1999, p. 10923-10930.*
Ito et al, Three NF-kB sites in the IkB-a promoter are required for induction of gene expression by TNFa, NAR, 1994, vol. 22(18), pp. 3787-3792.*
Idel et al, A20, a regulator of NFKB, maps to an atherosclerosis locus and differs between parental sensitive C57BL/6J and resistant FVB/N strains, PNAS, Nov. 25, 2003, vol. 100 (24), pp. 14235-14240.*
Ito et al, "Three NF-kappaβ sites in the Ikappaβ-alpha promoter are required for induction of gene expression by TNFalpha", Nuclei Acids Research, vol. 22, No. 18, Sep. 1994, pp. 3787-3792.
Delerive et al, "Induction of Ikappaβalpha expression as a mechanism contributing to the anti-inflammatory activities of peroxisome proliferator-activated receptor-alpha activators", The Journal of Biological Chemistry, vol. 275, No. 4, Nov. 24, 2000, pp. 36703-36707.
Brasier et al, "Nonisotopic Assays for Reporter Gene Activity", Current Protocols in Molecular Biology (1995) 9.7.12-9.7.21.
Kingston et al, "Isotopic Assays for Reporter Gene Activity", Current Protocols in Molecular Biology (1995) 9.7.1-9.7.11.

(Continued)

*Primary Examiner*—Maria Marvich
(74) *Attorney, Agent, or Firm*—Nixon & Vanderhye P.C.

(57) ABSTRACT

The present invention concerns a method for identifying substances useful for treating inflammation, characterized in that it comprises the following steps: (a) placing said substance in contact with a nucleic acid construct containing the Retinoid-Related Orphan Receptor (ROR) receptor response element of the promoter of the IκBα gene, under conditions suitable for allowing said substance to bind to said response element, (b) measuring the possible binding of said substance to the response element or the transcriptional activity of the response element or of a promoter containing it, (c) optionally comparing the measurement of step (b) with a measurement carried out under conditions similar to those of steps (a) and (b) but with a nucleic acid construct containing the mutated response element.

14 Claims, 6 Drawing Sheets

OTHER PUBLICATIONS

Kain et al, "Uses of Fusion Genes in Mammalian Transfection", Current Protocols in Molecular Biology (1996) 9.6.1-9.6.12.

Widmer et al, "Genomic Cloning and Promoter Analysis of Macrophage Inflammatory Protein (MIP)-2, MIP-1α, and MIP-1β, Members of the Chemokine Superfamily of Proinflammatory Cytokines[1]", The Journal of Immunology, vol. 150, No. 11, Jun. 1, 1993, pp. 4996-5012.

Roder et al, "FIRE3 in the promoter of the rat fatty acid synthase (FAS) gene binds the ubiquitous transcription factors CBF and USF but does not mediate an insulin response in a rat hepatoma cell line", Eur. J. Biochem. 260, 743-751 (1999).

Perkins et al, "Distinct combinations of NF-kB subunits determine the specificity of transcriptional activation", Proc. Natl. Acad. Sci., vol. 89, pp. 1529-1533, Mar. 1992.

Li et al, "Molecular Beacons: A Novel Approach to Detect Protein—DNA Interactions", Angew. Chem. Int. Ed. 2000, 39, No. 6, pp. 1049-1052.

Jobin et al, "The Ikappa B/NF-kappa B system: a key determinant of mucosal inflammation and protection", Am J Physiol Cell Physiol 278:451-462, 2000.

Israel, IkB kinase all zipped up, Nature, vol. 388, Aug. 7, 1997, pp. 519-521.

Yan et al, "Characterization of the Response Element and DNA Binding Properties of the Nuclear Orphan Receptor Germ Cell Nuclear Factor/Retinoid Receptor-related Testis-associated Receptor", The Journal of Biological Chemistry, vol. 272, No. 16, Apr. 18, 1997 pp. 10565-10572.

Thurberg et al, "The nuclear factor-[kappa]B/inhibitor of kappa B autoregulatory system and atherosclerosis", Current Opinion in Lipidology, vol. 9(5), Oct. 1998, pp. 387-396.

Perry et al, "Cloning of Interferon-Stimulated Gene 17: The Promoter and Nuclear Proteins that Regulate Transcription", Molecular Endocrinology 13:1197-1206, 1999.

McLaughlin et al, "Characterisation of the tumour necrosis factor (TNF)-α response elements in the human ICAM-2 promoter", Journal of Cell Science 112, 4695-4703, 1999.

Kouba et al, "Nuclear Factor-kB Mediates TNF-α Inhibitory Effect on α2(I) Collagen (COL1A2) Gene Transcription in Human Dermal Fibroblasts[1]", The Journal of Immunology, 1999, 162:4226-4234.

Collart et al, Regulation of Tumor Necrosis Factor Alpha Transcription in Macrophages: Involvement of Four kB-Like Motifs and of Constitutive and Inducible Forms of NF-kB, Molecular and Cellular Biology, vol. 10, No. 4, Apr. 1990, p. 1498-1506.

Fujita et al, "Independent modes of transcriptional activation by the p50 and p65 subunits of NF-kappa B", Genes & Dev. 1992 6:775-787.

Hiscott et al, "Characterization of a Functional NF-kB Site in the Human Interleukin 1β Promoter: Evidence for a Positive Autoregulatory Loop", Molecular and Cellular Biology, Oct. 1993, vol. 13, No. 10, pp. 6231-6240.

Brand et al, "Role of nuclear factor-kappa B in atherogenesis", Experimental Physiology, 1997; 82:297-304.

Collins et al, "Transcriptional regulation of endothelial cell adhesion molecules: NF-kB and cytokine-inducible enhancers", FASEB J. 9, 899-909 (1995).

Kopmels et al, "Evidence for a Hyperexcitability State of Staggerer Mutant Mice Macrophages", Journal of Neurochemistry, 58, 192-199 (1992).

Jetten, Recent Advances in the Mechanisms of Action and Physiological Functions of the Retinoid-Related Orphan Receptors (RORs), Current Drug Targets—Inflammation & Allergy, 2004, 3, 395-412.

Jetten et al, "The ROR Nuclear Orphan Receptor Subfamily: Critical Regulators of Multiple Biological Processes", 2001, pp. 206-247, Prog Nucleic Acid Res Mol Biol.

Nichols et al, "Role of Nuclear Factor-Kappa B (NF-kB) in Inflammation, Periodontitis, and Atherogenesis", Ann Periodontol vol. 6, No. 1, Dec. 2001; 6:20-29.

* cited by examiner

SEQUENCE LISTING

<160> NUMBER OF SEQ ID NOS: 15

<210> SEQ ID NO 1
<211> LENGTH: 22
<212> TYPE: DNA
<213> ORGANISM: Homo sapiens

<400> SEQUENCE: 1
gagcacaatg taggtcagat ag                                          22

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 2
gtcagcagct tctacctgga c                                           21

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 3
gtgttgttct gagagtgaaa ggcacg                                      26

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 4
atgcagcccc gaatgctcct catcgtggcc                                  30

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 5
ttcttggagg ccatgtgggc cat                                         23

<210> SEQ ID NO 6
<211> LENGTH: 8
<212> TYPE: DNA
<213> ORGANISM: Artificial Sequence
<220> FEATURE:
<223> OTHER INFORMATION: Description of Artificial Sequence: site ROR

<400> SEQUENCE: 6 taggtcag                                                          8

<210> SEQ ID NO 7
<211> LENGTH: 10
<212> TYPE: DNA
<213> ORGANISM: Artificial Sequence

```
<220> FEATURE:
<223> OTHER INFORMATION: Description of Artificial Sequence: site ROR

<400> SEQUENCE: 7
gtaggtcaga                                                              10

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: site ROR

<400> SEQUENCE: 8
atgtaggtca gata                                                         14

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: mutated ROR
      site

<400> SEQUENCE: 9
gagcacaatg tatttcagat ag                                                22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: mutated ROR
      site

<400> SEQUENCE: 10
gagcacaatg taaatcagat ag                                                22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: mutated ROR
      site

<400> SEQUENCE: 11
gagcacaatg tacatcagat ag                                                22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: mutated ROR
      site

<400> SEQUENCE: 12
gagcacaatg taactcagat ag                                                22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: mutated ROR
      site
```

```
<400> SEQUENCE: 13
gagcacaatg tatatcagat ag                                              22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: mutated ROR
      site

<400> SEQUENCE: 14
gagcacaatg taattcagat ag                                              22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: mutated ROR
      site

<400> SEQUENCE: 15
gagcacaatg tacctcagat ag                                              22
```

METHOD FOR IDENTIFYING SUBSTANCES USEFUL FOR TREATING INFLAMMATION USING THE RESPONSE ELEMENT TO THE IKBALPHA ROR RECEPTOR

This application is the US national phase of international application PCT/FR01/02652 filed 22 Aug. 2001 which designated the U.S.

The present invention relates to the use of the ROR receptor response element of the IκBα gene, and more specifically the sequence −910/−898 of the promoter of this gene, for screening substances useful for treating or preventing inflammation. In a particular embodiment, the invention concerns the use of a ROR receptor and/or at least one response element thereof or a functional equivalent thereof for screening substances useful for treating or preventing inflammation.

The NF-κB complex is composed of a wide variety of protein dimers from the NF-κB/ReI family. Five proteins from this family have been identified in mammals: NF-κB1 (p50 and its precursor p105), NF-κB2 (p52 and its precursor p100), c-ReI, ReIA/p65 and ReIB (Ghosh, S. et al., Ann. Rev. Immunol. 1998, 16: 225-60). All these proteins contain a highly conserved domain, called RHD for ReI Homology Domain, composed of about 300 amino acids with two "Ig-like" domains. This RHD domain is involved in the dimerization of NF-κB proteins, binding to DNA, and interaction with IκBs proteins and it posseses a nuclear localization signal (NLS). NF-κB dimers display different affinities for recognizing the consensus sequence GGGRNNYYCC, wherein R is a purine base, Y a pyrimidine base and N any base (Miyamoto, S. Verma, I. M., Adv. Cancer Res. 1995, 66: 255-92). Proteins from the NF-κB/ReI family also show different abilities for activating transcription; only the p65 and c-ReI proteins are capable of doing so, although ReIB activates transcription in certain cell types. Knocking out genes encoding the different proteins in this family has revealed different functions specific of each of its members. The p50/p65 heterodimer was the first dimer to be identified and it is the most abundant in the majority of cell types.

The NF-κB pathway regulates the transcription of a large number of genes involved in the immune and inflammatory response (Bauerle, P. A. and Baichwal, V. R., Adv. Immunol. 1997, 65: 111-37; Barnes, P. J. and Karin, M., N. Engl. J. Med. 1997, Ap 10, 336 (15): 1066-71; Siebenlist, U. et al., Ann. Rev. Cell Biol. 1994, 10: 405-55). A deregulation of this signalling pathway underlies many diseases such as cancer, neurodegenerative disorders, arthritis and asthma.

The NF-κB signalling pathway is activated by a broad spectrum of stimuli: cytokines (TNFα, IL-1), mitogens, lipopolysaccharide, viruses, viral proteins, double stranded RNA, physical and chemical stresses (Ghosh, S. et al., Ann. Rev. Immunol. 1998, 16: 225-60; Siebenlist, U. et al., Ann. Rev. Cell Biol. 1994, 10: 405-55).

In the majority of inactivated cells, NF-κB is present as an inactive cytoplasmic complex in which it is bound to an inhibitory protein IκB (Forman B. M. and Baltimore, D., Science 1998, 242: 540-546). Activation of NF-κB occurs through activation of an IκB kinase (IKK) which phosphorylates the IκBα protein at serine 32 and serine 36, leading to degradation of IκBα and release of NF-κB p52 and p65 proteins (Bauerle, P. A. and Baltimore D., Cell 1996, 87: 13-20; Verma, I. M., Stevenson, J. K., Schwartz, E. M., Van Antwerp, D. and Miyamoto, S., Genes & Dev. 1995, 9: 2723-2735). The NF-κB dimers thus released migrate to the nucleus where they regulate transcription.

The IκB family comprises the proteins IκBα, IκBβ, IκBγ, IκBε, Bcl-3, NF-κB1, NF-κB2 (Whiteside, S. T. and Israel, A., Semin. Cancer Biol. 1997, Apr 8(2): 75-82). IκB proteins are involved in the terminal stage of the NF-κB signalling pathway since these newly synthesized proteins are directed to the nucleus where they interact with DNA-bound NF-κB complexes, causing dissociation from the binding site and translocation back into the cytoplasm (Arenzana-Seeisdedos, F. et al., J. Cell Sci. 1997, Feb. 110: 369-78).

Expression of the IκBα protein is controlled by the NF-κB pathway which exerts feedback control of this signalling pathway (Sun, S. C. et al., Science 1993, Mar 26, 259 (5103): 1912-5). In addition, glucocorticoids also appear to control IκBα expression (Auphan, N. et al., 1995, Oct. 13, 270 (5234): 286-90; Scheinman, R. I., 1995, Oct. 13, 270 (5234): 283-6), while estrogens reduce expression levels (Sun S. C. et al., Science 1993, Mar. 26, 259 (5103): 1912-5). Lastly, functional analysis of the IκBα promoter has revealed the critical role of an AP-1 binding site (Kralova, J. et al., Oncogene 1996, Jun. 20, 12 (12): 2595-604) and an SP1 binding site (Algarte, M. et al., Mol. Cell Biol., 1999, Sep. 19 (9): 64140-53).

The RORα receptor (Retinoid-related orphan receptor alpha) (NR1F1) is a member of the nuclear receptor family which binds as a monomer, via an RORE response element composed of a single 6 base pair sequence with the hemipalindromic motif AGGTCA preceded by an A/T-rich region (Giguère, V., McBroom, L. B. D. and Flock, G., Mol. Cell. Biol., 1995, 15: 2517-2526; McBroom, L. B. D., Flock, G. and Giguère, V., Mol. Cell. Biol., 1995, 15: 796-808). Under certain conditions RORα can also bind to DNA in homodimeric form via a response element composed of a repetition of two hemipalindromic motifs AGGTCA separated by two nucleotides and preceded by an A/T-rich region (Harding, H. P. et al., Mol. Endocrinol. 1997, Oct. 11 (11): 1737-46).

RORE sites are ROR response elements on which the ROR receptor binds to modulate the transcriptional activity of the gene situated downstream. Such sites may be used to confer ROR sensitivity to a heterologous promoter.

The RORα gene has four isoforms sharing a common DNA binding domain (DBD) as well as a common ligand binding domain (LBD). These isoforms differ at their amino terminus (Giguère, V. et al., Genes & Dev. 1994, 8: 538-553). RORα-deficient mice display cerebral defects (ataxia) characteristic of staggerer mice, which harbor a deletion in the RORα gene that creates a truncated protein unable to bind DNA (Hamilton, B. A. et al., Nature 1996, 379: 736-739†; D'Ambrosio, D. et al., J. Clin. Invest. 1998, 101: 252-262; Dussault, I., Fawcett, D., Mathyssen, A., Bader, J.-A. and Giguère, V., Mech. Dev. 1998, 70: 147-153; Steinmayr, M. et al., J. Biol. Chem. 1998, 95: 3960-3965). Furthermore, staggerer mice overproduce IL-1 (Kopmels, B. et al., J. Neurochem. 1992, 58: 192-199).

It has been shown in the prior art that staggerer mice bearing a mutation in the RORα gene (mutation which prevents translation of the DNA binding domain) have immune defects such as hyperproduction of IL-1α in macrophages (Kopmels, B. et al., J. Neurochem. 1992, 58: 192-199; Kopmels, B. et al., J. Neurochem. 1990, 55: 1980-1985).

In another study, the RORα receptor, which belongs to the orphan nuclear receptor family, was reported to be activated by CGP 52608, a thiazolidinedione derivative, in Drosophila SL3 cells (Wiesenberg, I. et al., Mol. Pharmacol. 1998, 53: 1131-1138). This study also showed that CGP 52608 exerts anti-arthritic activity in vivo. However, it did not provide any evidence demonstrating that the anti-inflammatory activity of CGP 52608 is ROR-dependent in mammalian cells.

It has also been suggested, based solely on the presence of an ROR response element in its promoter, that the gene encoding 5-lipoxygenase, an important enzyme involved in the control of inflammation and allergy, is a target of RORα (Steinhilber et al., J. Biol. Chem. 1995, 270 (13): 7037-7040).

The research carried out within the scope of the present invention has revealed a new function of the RORα1 receptor. In a surprising manner, the inventors demonstrated for the first time that RORα negatively regulates the inflammatory response by interfering with the NF-κB pathway. In fact, it has now been shown that transcription of the IKBα protein, the main inhibitor of the NF-κB pathway, is activated by RORα via a new RORE response element, identified in the promoter of the IKBα gene. This response element is a perfect RORE consensus site and is located between positions −910/-898 of the IKBα promoter, the site having the sequence gagcacAATGTAGGTCAgatag (SEQ ID NO:1) (Ito, C.Y., Kazantsev, A.G. and Baldwin, A.S., Nucl. Acid Res. 1994, 22: 3787-3792).

Moreover, the inventors showed that mutation of this sequence results in a loss of effect of RORα1, illustrating its functional importance. Any other nuclear receptor or any other substance which binds to this sequence can therefore modulate IκBα expression.

Now, by binding to nuclear factor NF-κB, the IκBα protein forms an inactive complex (IκBα-NF-κB) which prevents the activation of expression of pro-inflammatory genes such as the genes encoding certain cytokines or the COX-2 gene. These data demonstrate that RORα1 or any other nuclear factor that binds to the sequence −910/−898 of the IκBα promoter is a potential target for treating chronic inflammatory disorders.

Figure 1:
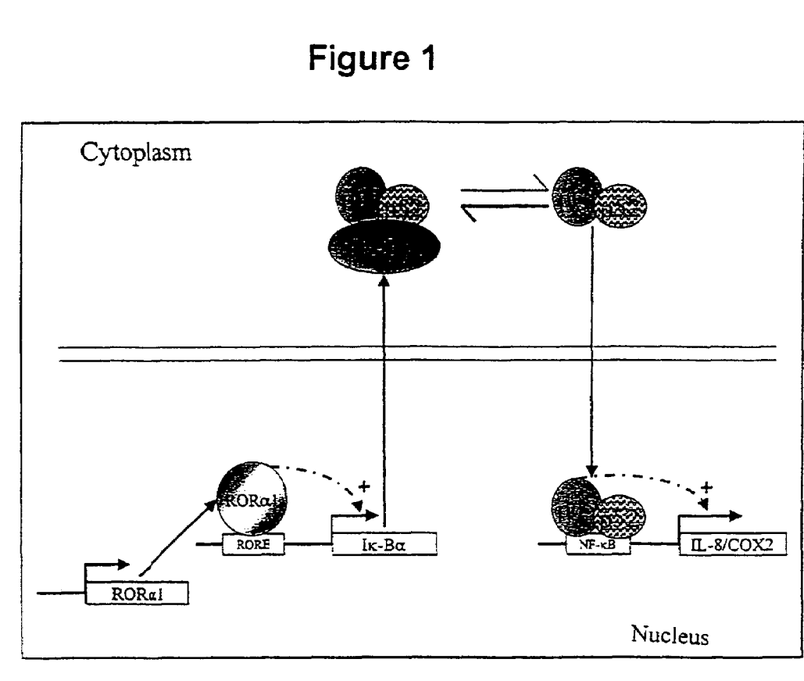
FIG. 1 outlines the mechanisms involved in the regulation of the inflammatory response identified in the present invention

FIG. 1, attached, outlines the mechanisms involved in regulation of the inflammatory response identified in the present invention.

Demonstration of the role of sequence −910/−898 has therefore allowed the development of new methods for identifying substances useful for treating human (chronic) inflammatory disorders such as atherosclerosis or rheumatoid arthritis. It is understood that the sequence identified in the invention can also be used for identifying new nuclear factors which affect the activity of the IκB promoter through this sequence and, consequently, may be useful for treating human (chronic) inflammatory disorders such as atherosclerosis or rheumatoid arthritis.

Identification of IκBα as a target of RORα1 has therefore equally allowed the development of new methods for identifying substances useful for treating human (chronic) inflammatory disorders such as atherosclerosis or rheumatoid arthritis.

An object of the present invention therefore resides in a method for identifying substances useful for treating inflammation, wherein said method comprises the following steps:

a) placing said substance in contact with a nucleic acid construct containing the ROR receptor response element of the promoter of the IκBα gene, under conditions suitable for allowing said substance to bind said response element, b) measuring the possible binding of said substance to the response element or the transcriptional activity of the response element or of a promoter containing it, c) optionally comparing the measurement of step (b) with a measurement carried out under the same conditions as steps (a) and (b) but with a nucleic acid construct containing the mutated response element.

The response element is preferably the RORα receptor response element and preferably the hRORα receptor.

According to a specific embodiment of the invention, the conditions allowing said substance to bind said response element comprise the presence of the ROR receptor or a functional equivalent thereof.

Thus, the method of the invention comprises the following steps:

a) placing said substance in contact with the ROR receptor or a functional equivalent thereof and a nucleic acid construct containing the response element to said receptor of the IκBα gene promoter, under conditions suitable for allowing said receptor or its functional equivalent, said substance or complex formed of the receptor or its functional equivalent and said substance, to bind to said response element, b) measuring the possible binding of the ROR receptor or its functional equivalent, of the substance or a complex formed of the ROR receptor or its functional equivalent and said substance, to the response element or the transcriptional activity of the response element or of a promoter containing it, c) optionally comparing the measurement of step (b) with a measurement carried out under the same conditions as steps (a) and (b) but with a nucleic acid construct containing the mutated response element.

Functional equivalent of the ROR receptor is understood to mean any nuclear factor able to bind to the ROR receptor response element of the promoter of the IκBα gene. This therefore comprises any protein simultaneously containing:

a binding site having a selectivity similar to that of ROR for a given ligand of the latter and, a DNA binding site recognizing the same response element as ROR or a response element having a similar nucleic acid sequence.

The term "functional equivalent" which refers to the ROR receptor generally designates any polypeptide derived from the structure of the ROR receptor and retaining the ability to bind to the response element of the IκBα gene, particularly any response element having the sequence SEQ. ID. NO: 1 or functional variants thereof. The functional equivalents may be natural variants (polymorphism, splicing, etc.), fragments, mutants, deletants, etc. Preferably, they are polypeptides comprising at least one amino acid region having at least 60% identity, preferably at least 75% and even more preferably at least 90 or 95%, to that of the ROR receptor, particularly RORα, preferably hRORα. The term further includes polypeptides containing the DNA binding site of the ROR receptor.

Thus, within the context of the present invention, the ROR receptor refers to all the isoforms α, β and γ of the ROR family. The RORα receptor is more particularly preferred and the hRORα receptor is even more preferred.

A functional equivalent of the ROR receptor may also be a nuclear factor identified by the method of the invention described hereinabove.

An advantageous embodiment of the method of the invention consists in using in step (a) a nucleic acid construct which contains several copies of the RORα response element and preferably the hRORα receptor of the IκBα gene promoter. For instance the contruct may contain 1 to 10 copies of the RORα receptor response element, typically 1 to 5 copies.

An advantageous embodiment of the method of the invention consists in using in step (a) a nucleic acid construct comprising all or part of the IκBα gene promoter containing the ROR receptor response element.

A preferred example of a nucleic acid construct according to step (a) comprises or is constituted by the sequence between positions −910/−898 of the IκBα promoter which has the following sequence:

GAGCACAATGT<u>AGGTCAG</u>ATAG    (SEQ ID No: 1)

or a fragment thereof containing but not restricted to the 6 base pair consensus sequence underlined above. Examples of ROR receptor response element constructs that may be used in the invention comprise the following specific sequences:

T<u>AGGTCAG</u>    (SEQ ID NO: 6)

GT<u>AGGTCAG</u>A    (SEQ ID NO: 7)

ATGT<u>AGGTCAG</u>ATA    (SEQ ID NO: 8)

In a particular embodiment, a nucleic acid is used comprising the entire sequence SEQ ID NO: 1. Compared with the 6 base pair consensus sequence alone underlined in SEQ ID No: 1 hereinabove, this sequence has the advantage of including one or more regions involved in interactions with nuclear factors.

The possible binding of the substance, the ROR receptor or a complex formed of the ROR receptor and said substance to the response element may be measured by any method known to those skilled in the art, for instance by detecting a signal produced by the response element following said binding. These may be any direct or indirect methods, such as those which use a reporter gene, binding tests, etc.

Thus, a preferred embodiment of the invention consists in using a nucleic acid construct combining the response element of the IκBα gene with a reporter gene. In an advantageous manner, said reporter gene is placed under the control of a promoter containing at least one copy of said response element.

The reporter gene may therefore be placed under the control of any promoter whose sequence comprises the sequence SEQ. ID. NO: 1 or a functional variant thereof. Such specific sequence may be present in one or more copies in the promoter (preferably 1 to 10 and even more preferably 1 to 6), upstream, downstream or internally, in the same orientation or in the opposite orientation. In a preferred embodiment of the invention, the reporter gene is placed under the control of a promoter comprising one or more copies of the sequence SEQ ID NO: 1 or a fragment thereof containing at least the consensus region. It is preferably a promoter having differential activity in the absence and presence of ROR or a functional equivalent which can be detected.

To create a promoter according to the invention, the ROR receptor response element may be associated with a transcriptional minimal promoter. The minimal promoter is a transcriptional promoter having a low or nonexistent basal activity, and which can be increased in the presence of a transcriptional activator (e.g. ROR). A minimal promoter may therefore be a naturally weak promoter in mammalian cells, i.e. producing a non-toxic and/or insufficient expression to cause a marked biological effect. In an advantageous manner, a minimal promoter is a construct prepared from a native promoter, by deleting region(s) that are not essential for transcriptional activity. For instance, it is preferably a promoter comprising principally a TATA box, generally less than 160 nucleotides in size, centered around the transcription initiation codon. A minimal promoter may thus be prepared from strong or weak viral or cellular promoters, such as for example the promoter of the herpes virus thymidine kinase (TK) gene, the CMV early promoter, the PGK promoter, the SV40 promoter, etc.

In a preferred embodiment, the reporter gene is placed under the control of the promoter of the IκBα gene.

Any reporter gene allowing to measure the activity of nuclear receptors on the sequence comprising their response element may be used in the screening method according to the invention. These are exemplified for instance by the chloramphenicol acetyltransferase (CAT) gene, the firefly (Luc) or Renilla (Ren) luciferase gene, the secreted alkaline phosphatase gene (SAP) or that of beta-galactosidase (β-Gal) and the IκBα gene itself.

The activity of the proteins encoded by these genes can be easily measured by conventional methods and gives an indirect idea of the effect of the nuclear receptors on gene expression by measuring the amount of proteins produced and/or their enzymatic activity.

According to a more particular embodiment of the invention, the reporter gene is the IκBα gene. In this case, the accumulation of IκBα protein can be measured by its ability to bind NF-κB or to inhibit its action for example by using a reporter vector comprising several NF-κB response elements cloned upstream of a reporter gene.

The use of a reporter gene has the advantage of verifying whether the receptor or a functional equivalent thereof or said substance is able not only to bind, alone or complexed with the ROR receptor, to said response element, but also to increase the transcriptional activity of the response element or of a promoter containing said response element. In this manner the role of said substance in inhibiting the inflammatory response can be confirmed.

Advantageously, this ability to increase transcriptional activity may be measured at step (b) and possibly (c) on the IκB gene by any direct or indirect methods known to those skilled in the art, such as transfection, analysis of mRNA or protein in vitro and in in vitro and in vivo models.

An example of the method according to the invention comprises the following steps:

a) placing said substance in contact with a host cell transformed with a nucleic acid construct comprising at least a reporter gene functionally combined with the ROR receptor response element of the IκBα gene promoter as defined hereinabove, b) measuring the expression of the reporter gene by any suitable means, c) optionally comparing the measurement of step (b) with a measurement carried out under the same conditions as steps (a) and (b) but with a nucleic acid construct containing the mutated response element.

According to a specific embodiment of the hereinabove method, the host cell of step (a) expresses an ROR receptor or a functional equivalent thereof as defined hereinabove.

In step (c), comparison with the measurement of step (b) is advantageously carried out with a measurement under the same conditions as steps (a) and (b) but with a nucleic acid construct containing the mutated response element, i.e. an ROR response element whose sequence has been altered so as to make it unable to bind the ROR receptor in a functional manner. Such mutated response element advantageously has the following sequence GAGCACAATGTXXXXXX-GATAG (SEQ ID NO:16), wherein X is chosen from among A, T, C, G.

As a non-limiting example, the following mutated sequences are preferred:

GAGCACAATGTATTTCAGATAG    (SEQ ID NO: 9)

GAGCACAATGTAAATCAGATAG    (SEQ ID NO: 10)

```
                        -continued
GAGCACAATGTACATCAGATAG       (SEQ ID NO: 11)

GAGCACAATGTAACTCAGATAG       (SEQ ID NO: 12)

GAGCACAATGTATATCAGATAG       (SEQ ID NO: 13)

GAGCACAATGTAATTCAGATAG       (SEQ ID NO: 14)

GAGCACAATGTACCTCAGATAG       (SEQ ID NO: 15)
```

The substances that can be identified by the method according to the invention may be chemical or biological compounds. For instance, they may be nuclear factors.

Furthermore, classical methods for identifying clones encoding DNA-binding proteins may be used in the method of the invention. For example, it is possible to use the screening of a λgt11 expression library (Ausubel et al., Current Protocols in Molecular Biology, John Wiley & Sons, Inc. 1997), purification by affinity chromatography followed by sequencing the protein (Ausubel et al., Current Protocols in Molecular Biology, John Wiley & Sons, Inc. 1997), the so-called "one-hybrid" method (Wang, M. M., Nature 1993, Jul. 8, 364 (6433): 121-6), or yet the so-called "phage display" method (Smith, G. P. and Scott, J. K., Methods Enzymol. 1993, 217†: 228-57; O'Neil, K. T. and Hoess, R. T., Curr. Opin Struct. Biol. 1995, Aug. 5(4)†: 443-9).

The invention equally concerns a vector comprising at least one nucleic acid construct containing at least one copy of the response element of the IκBα gene mutated or not, able to be used in a method for identifying substances described hereinabove.

The invention further relates to the host cells containing such a vector.

Host cell is understood to mean any type of cell suitable for expressing the abovedescribed genes, such as in particular mammalian cells, bacteria or yeasts or even insect cells. In a preferred embodiment of the invention, the host cells are mammalian cells (hepatocytes, fibroblasts, endothelial cells, muscle cells, etc.). Even more preferably, such cells may be human cells. They may also be primary cultures or established cell lines. In another embodiment, it is further possible to use prokaryotic cells (bacteria), yeast cells (*Saccharomyces, Kluyveromyces,* etc.), plant cells, etc.

The substances may be placed in contact with the cells at different times, according to their effect(s), their concentration, the cell type and the technical factors.

The vectors used are, of course, suited to the type of cell being transfected, and include plasmids, viruses or artificial chromosomes.

The test substance may be placed in contact with the nucleic acid construct or cells on (or in) any suitable support and notably on a plate, in a tube or flask, a membrane, etc. In general, placing in contact occurs in a multiwell plate which makes it possible to conduct many different tests in parallel. Typical supports include microtitration plates and more particularly plates having 96 or 384 wells (or more) which are easy to manipulate.

Depending on the support and the nature of the test substance, different quantities of cells may be used to implement the described methods. Typically, $10^3$ to $10^6$ are placed in contact with a type of test substance, in a suitable culture medium, and preferably between $10^4$ and $10^5$ cells.

The quantity (or concentration) of test substance may be adjusted by the user according to the type of substance (its toxicity, its ability to penetrate the cells, etc.), the number of cells, the incubation time, etc. Generally, the cells are exposed to quantities of test substance ranging from 1 nM to 1 mM. Of course other concentrations may be tested without deviating from the present invention. Moreover, each substance may be tested in parallel at different concentrations. Also, different adjuvants and/or vectors and/or products that facilitate penetration of the substances inside the cells such as liposomes, cationic lipids or polymers may, furthermore, be used, where necessary. Contact time may range for example from a few minutes to a few hours or days, particularly between 5 and 72 hours, generally between 12 and 48 hours. The cells and the various reagents must preferably remain in contact long enough to allow de novo synthesis of the product expressed by the reporter gene or the interaction under study.

The invention equally concerns substances identified through the method of the invention with the exception of the ROR receptor itself.

The invention therefore also has as its object a pharmaceutical composition for preventing or treating inflammatory disorders, comprising as active principle at least one substance other than the ROR receptor that can bind, alone or complexed with the ROR receptor or a functional equivalent thereof, to the ROR receptor response element of the IκBα gene.

The invention more particularly concerns the use of a transcriptional activator of the IκBα gene for preparing a medicinal product intended to treat or prevent inflammatory disorders.

According to a particular manner of use according to the invention, the transcriptional activator of the IκBα gene is a substance able to bind alone or complexed with the ROR receptor to the response element to said ROR receptor of the IκBα gene. The transcriptional activator of the IκBα gene may therefore be an activator of the binding of RORα to the response element of the IκBα gene promoter or of its transcriptional activity.

The invention therefore relates more particularly to the use of a substance able to bind, alone or complexed with the ROR receptor or a functional equivalent thereof, to the IκBα gene promoter response element and to increase the expression of IκBα for preparing a medicinal product intended to treat or prevent inflammatory disorders.

Other advantages and features of the invention will become apparent in the following examples which refer to the attached figures wherein:

BRIEF DESCRIPTION OF DRAWINGS

The immunocytochemical studies were performed as described previously (Chinetti, G. et al., J. Biol. Chem. 1980, 273: 25573-25580) using a rabbit polyclonal RORα antibody directed against amino acids 163 to 225.

FIG. 4A shows PAC1A cells transfected with the reporter gene (NF-κB) 3-Luc (100 ng) in the presence of an RORα1 expression vector (pSG5-RORα1, 50 ng) or an empty vector (pSG5 control). Two hours post-transfection, cells were placed in DMEM medium supplemented with 0.2% FCS in the presence or absence of LPS (10 mg/ml) for 24 hours.

FIG. 4B shows primary smooth muscle cells infected with Ad-RORα1 or Ad-GFP for 16 hours, then stimulated with TNFα (10 ng/ml) for 0, 15, 30 and 60 minutes. Total (T; lower gel) and nuclear (N; upper gel) protein extracts were prepared and analyzed by Western blot using anti-p65 antibody (Santa Cruz).

FIG. 4C shows primary smooth muscle cells infected with Ad-RORα1 or Ad-GFP for 16 hours, then stimulated with TNFα (10 ng /ml) for 30 minutes. Nuclear protein extracts (5 mg) were prepared and analyzed by EMSA using NF-κB and Sp1 labelled probes (Promega). Complexes which migrated are indicated by an arrow. The double arrow shows the unbound probe.

FIG. 5A shows primary smooth muscle cells infected with Ad-RORα1 or Ad-GFP for 16 hours. Total RNA was prepared and IκBα and GAPDH mRNAs were measured by Northern blot.

FIG. 5B depicts PAC1A cells transfected with fragments of the IκBα promoter (100 ng) in the presence of pSG5-RORα1 or empty vector (pSG5, 50 ng).

RORα1, but not RORα2 or RORα3, binds to an RORE site within the IκBα promoter.

FIG. 6A shows PAC1A cells transfected with the reporter vector (IκBα-RORE) 2-TK-Luc (100 ng) in the presence of RORα1, RORα2 or RORα3 (50 ng) or empty vector pSG5 (50 ng).

FIG. 6B shows PAC1A cells transfected with the reporter vector (IκBα-RORE) 2-TK-Luc (100 ng) in the presence of RORα1 (50 ng), RORα1Δ235 or empty vector (50 ng).

FIG. 6C depicts the gel shift experiments conducted by using the in vitro translated RORαl protein (TNT-T7 Promega) and an IκBα-RORE labelled probe. Increasing concentrations (1×, 10× and 100×) of the native (AGGTCA) or mutated (ACCTCA) oligonucleotide competitor were used to demonstrate the specificity of the migrating complex. To enhance the mobility of the complex, 1 μl of RORα1 antibody was added to the binding reaction (S: shift of the complex; SS: super-shift of the complex; FP: unbound probe).

I—Materials and Methods

1) Cell Culture

Human aorta smooth muscle cells (PromoCell, Heidelberg, Germany) and human coronary artery endothelial cells (Clonetics) were maintained in primary culture in the usual conditions. Cells were used between passages 5 to 8. Human macrophages and monocytes were prepared and maintained in primary culture as described previously.

2) RNA Analysis

RNAs were prepared and analyzed by Northern blot as described previously using fragments of IκBα and GAPDH cDNA as probes. For the RT-PCR analysis of RORα expression, total RNA was transcribed by reverse transcriptase and then amplified by PCR using the following primers:

for RORα, 5'-GTCAGCAGCTTCTACCTGGAC-3' (SEQ ID No: 2) and 5'-GTGTTGTTCTGAGAGTGAAAG-GCACG-3' (SEQ ID No: 3) (fragment size: 482 bp);

for GAPDH, 5'-ATGCAGCCCCGAATGCTCCT-CATCGTGGCC-3' (SEQ ID No: 4) and 5'-TTCTTG-GAGGCCATGTGGGCCAT-3' (SEQ ID No: 5) (fragment size: 239 bp)

3) Adenovirus Production

Recombinant adenoviruses Ad-GFP and Ad-RORα1 were obtained by homologous recombination in *E. coli* after inserting the cDNAs in the vector pADCMV2. Stocks of viral particles were obtained as previously described. The titer of the suspension was determined by counting lytic plaques after infection of 293 cells and defined as pfu/ml. Cells were infected at a multiplicity of infection of 100 viral particles per cell by adding the viral stocks directly to the smooth muscle cell culture medium.

4) Plasmids and Transient Transfection

The expression vectors pSG5-hRORα1, -hRORα2, -hRORα3 and -RORαΔ235 were derived from pCMX vectors described previously. A fragment corresponding to the region −929 /+22 of the IκBα promoter was amplified from human genomic DNA and cloned into Promega basic pGL2 plasmid to give the construct p(−922/+22) IκBα Luc. The mutation of the ROR site present in this fragment (AGGTCA mutated to ACCTCA) was introduced by site directed mutagenesis (Stratagene). The reporter vector p(−385/+22) IκBα was a kind gift of Dr. Israel (Pasteur Institute, Paris). The reporter vector (IκBα-RORE) 2-Tk-Luc was created by inserting two copies of the RORE site of the IκBα promoter upstream of the minimal promoter of the herpes simplex virus thymidine kinase gene. The construct (NF-κB) 3-Luc was obtained from Stratagene. PAC1A cells (rat aorta smooth muscle cell line) were transfected using a cationic lipid as previously described.

II—Results

Considering that chronic inflammation is a feature of atherosclerosis (Ross, R., New Engl. J. Med. 1999, 340: 115-126) and that staggerer mice have a pro-inflammatory profile, the inventors measured ROR expression in the different types of cells in the vascular wall by RT-PCR.

Figure 2A:
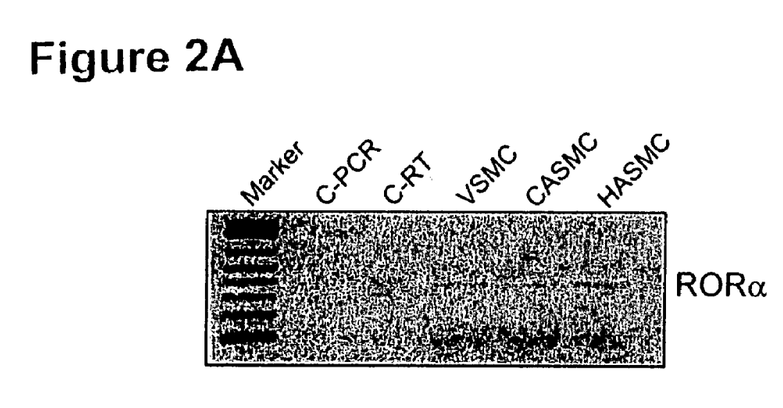
FIGS. 2A and 2B depict RORα expression in different types of cells in the vascular wall based on RT-PCR analysis (35 cycles) of RORα (FIG. 2A) and GAPDH (FIG. 2B) mRNA (C-PCR and C-RT are negative controls for the PCR and RT, respectively).
Figure 2B:
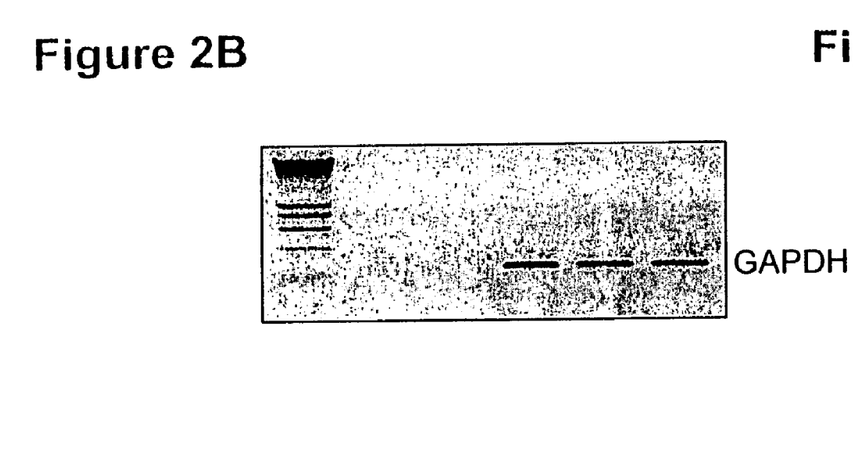

RORα expression was detected in endothelial cells, smooth muscle cells (SMC) and monocytes (FIG. 2A). On the other hand, RORα expression was found to be much lower in monocyte-derived macrophages.

Figure 2C:
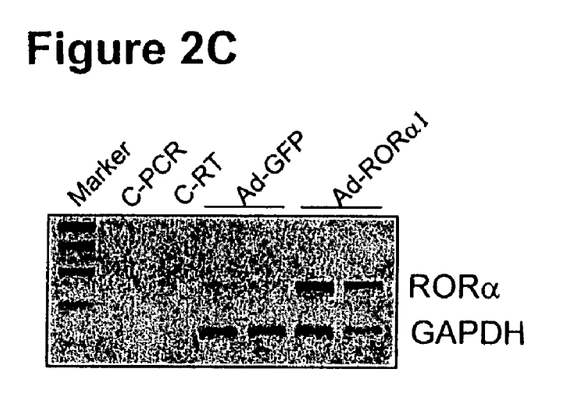
FIG. 2C shows the RT-PCR analysis of RORα mRNA in smooth muscle cells after a 24 hour infection with Ad-RORα1 or Ad-GFP.
Figure 2D:
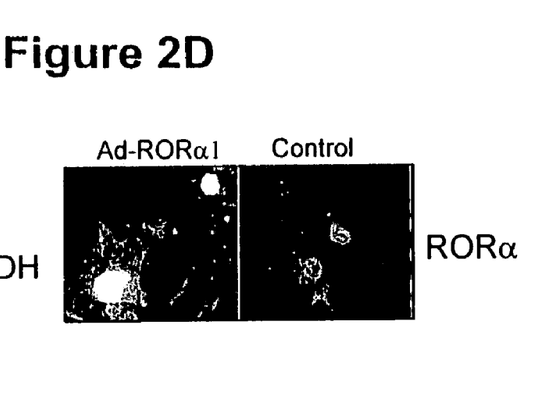
FIG. 2D illustrates the analysis of RORα protein expression in smooth muscle cells infected for 24 hours with or without Ad-RORα1.

To examine the potential role of RORα in regulating the inflammatory response, the inventors generated by homologous recombination an adenovirus vector encoding the RORα1 isoform, which is preponderant (Forman, B. M et al., Mol. Endocrin. 1994, 8: 1253-1261). Infection of primary SMC with Ad-RORα1 induced the expression of RORα, whereas infection with Ad-GFP used as negative control had no effect on endogenous levels (FIG. 2C). The immunocytochemical studies with a polyclonal anti-RORα antibody (aminoacids 163-225) confirmed these results at the protein level and furthermore demonstrated that both endogenous RORα and exogenous RORα are localized primarily in the nucleus (FIG. 2D).

The effects of RORα1 on the different markers of the vascular inflammatory response induced by TNFα were then investigated.

Figure 3A:
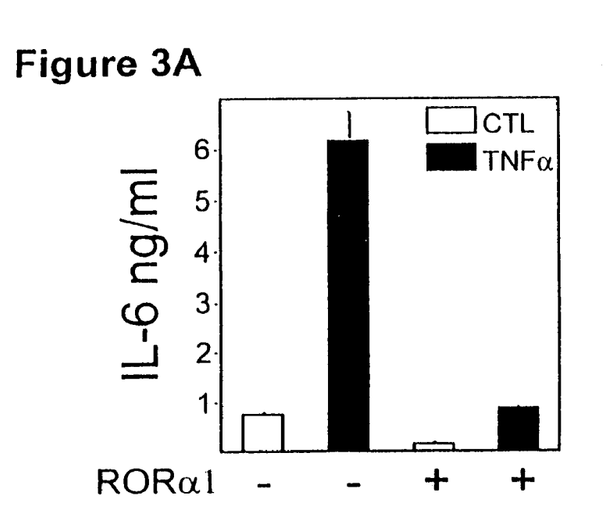
FIGS. 3A and 3B show that RORα1 inhibits the secretion of IL-6 (FIG. 3A), IL-8 (FIG. 3B) and COX-2 expression induced by TNFα in smooth muscle cells. Primary smooth muscle cells were infected with Ad-RORα1 or Ad-GFP virus for 16 hours, then subjected to 24 hour stimulation with TNFα (10 ng/ml). After this treatment, IL-6 and IL-8 concentrations in the medium were determined by ELISA (R&D Systems UK).
Figure 3B:
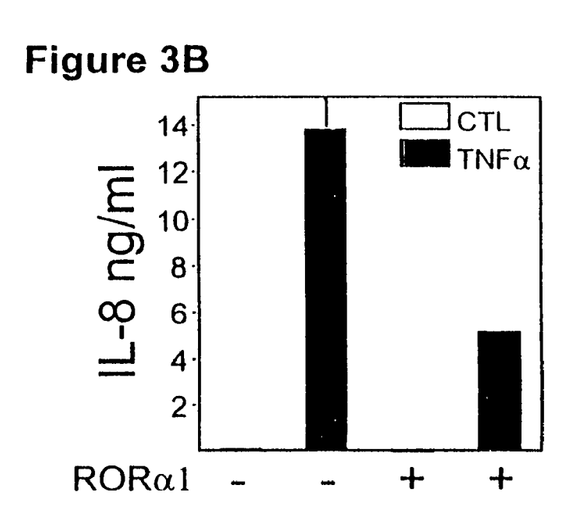
Figures 3C, 3D:
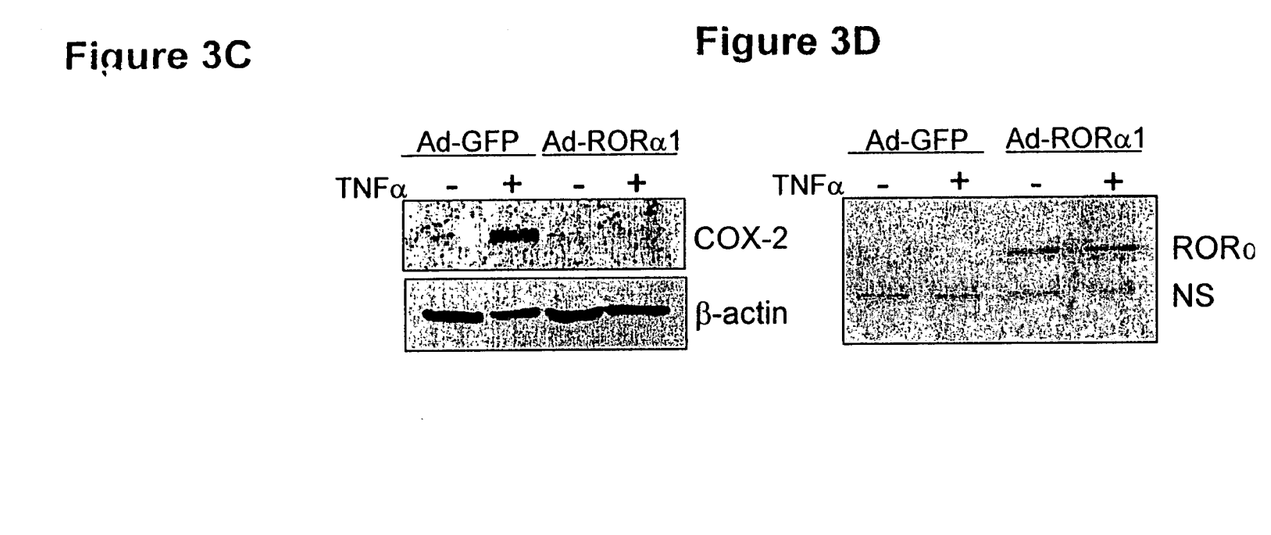
FIGS. 3C and 3D illustrate the expression of COX2 and RORα protein determined by Western blot analysis. COX2 protein levels were normalized to β-actin content in the cells (NS=nonspecific).

In the absence of stimulation, both IL-6 and IL-8 were detected in cells infected with Ad-GFP, an effect due to the immunogenicity of this construct. This weak induction was significantly inhibited by infection with Ad-RORα1 (FIGS. 3A and 3B). Treatment of Ad-GFP-infected cells with TNFα (24 h) led to a marked induction of both cytokines which could be significantly inhibited by infection with Ad-RORα1 (FIGS. 3A and 3B). Endogenous RORα protein was not detected in Ad-GFP-infected cells, which is undoubtedly due to the weak affinity of the antibody used. However, in cells infected with Ad-RORα1, RORα expression was increased, and the level was unaffected by TNFα stimulation (FIG. 3C). COX-2 protein levels were also measured in the same experiments. TNFα strongly induced COX-2 expression, an effect which was abolished in Ad-RORα1-infected cells (FIG. 3D). These data demonstrate that RORα1 negatively regulates the inflammatory response induced by TNFα in primary aorta smooth muscle cells.

Figure 4A:
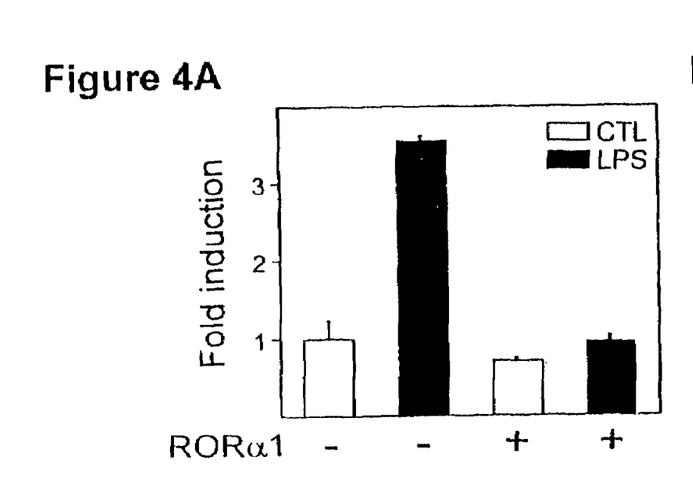
FIGS. 4A to 4C depict the inhibition of NF-κB activation by RORα1.

Within the scope of the research which led to the invention, PAC1A cells (rat smooth muscle cell line) were transiently transfected with a promoter under the control of the NF-κB pathway, in the presence or absence of RORα1. Considering that these cells do not respond to TNFα stimulation, the inventors used LPS as inducer of the NF-κB pathway. LPS treatment significantly increased (more than 3-fold) the activity of the promoter under NF-κB control. This induction was reduced in cells cotransfected with RORα1. Basal promoter activity was not significantly affected in these conditions (FIG. 4A). These results confirm that RORα1 exerts its anti-inflammatory effect by inhibiting the transcriptional activity of NF-κB.

Figure 4B:
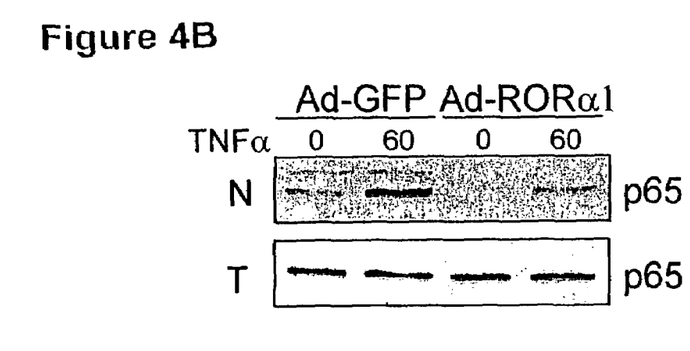
Figure 4C:
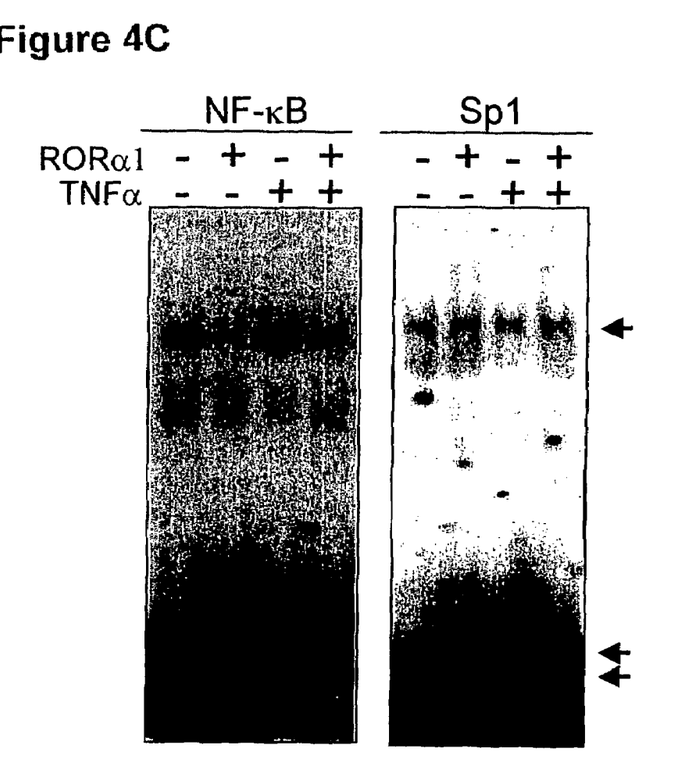

The inventors then investigated the effect of RORα1 overexpression on nuclear translocation of p65 by Western blot. They found that treatment with TNFα led to transient nuclear translocation of p65 in Ad-GFP-infected cells. This translocation was less pronounced in cells infected with Ad-RORα1, indicating that RORα1 controls p65 translocation without regulating the total expression of p65 protein (FIG. 4B). Gel shift experiments (EMSA) were conducted to examine the effects of this reduction of migration. Twenty-four hours post-infection, TNFα was added to the cells for 30 minutes. At the end of this treatment period, nuclear extracts were prepared and used to check for the presence of NF-κB proteins p50 and p65 by gel shift experiments using labelled probes whose sequences correspond to the NF-κB consensus site. Ad-GFP-infected cells displayed significantly lower binding activity to the NF-κB site than cells infected with Ad-RORα1, which is consistent with the previous results (FIGS. 3A and 3B). The inventors observed that TNFα stimulation led to a large increase in NF-κB binding to its response element, a binding which was strongly reduced in Ad-RORα1-infected cells. Neither TNFα, nor RORα1 overexpression had any effect on the binding of nuclear factors to an Sp1 probe (FIG. 4C), which indicates that the action of RORα1 is specific to the NF-κB pathway.

It is also known that many nuclear receptors inhibit transcription controlled by NF-κB and binding to the NF-κB site, by interacting with the p65 subunit (Göttlicher, M. Heck, S. and Herrlich, P., J. Mol. Med. 1998, 76: 480-489). For example, it was shown that cotransfection with p65 led to strong induction of an NF-κB-controlled promoter in PAC1A cells (data not shown). This induction was not affected by cotransfection with RORα1, indicating that, contrary to other nuclear receptors, RORα1 exerts a negative control of the NF-κB pathway without associating with p65.

Figure 5A:
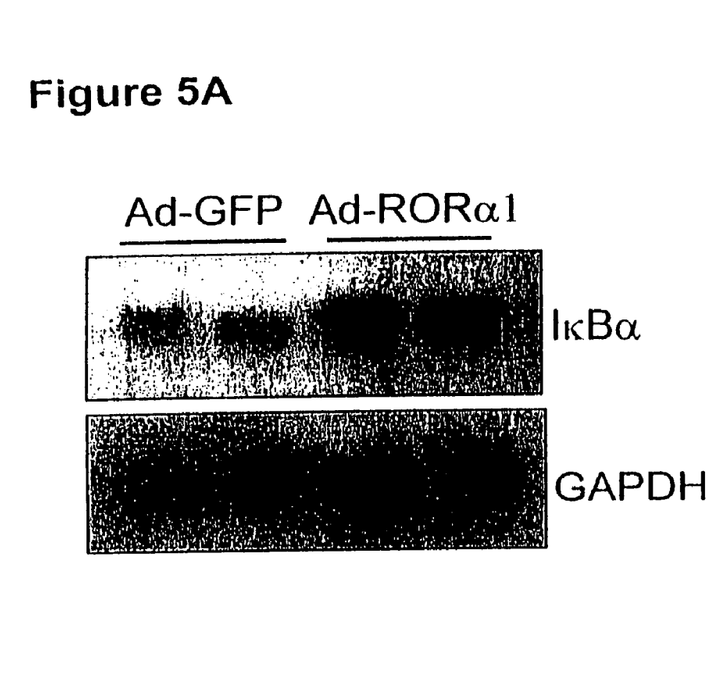
FIGS. 5A and 5B illustrate the induction of IκBα transcription by the RORα1 receptor in cells infected with an RORα expression vector (pSG5-RORα1).

In quiescent cells, the IκBα protein sequesters the p50/p65 heterodimer in the form of an inactive cytoplasmic complex. Considering that RORα inhibits p65 translocation and its subsequent binding to the NF-κB site, IκBα expression levels were determined in cells infected with Ad-GFP or with Ad-RORα1. Ad-GFP-infected cells expressed low levels of IκBα mRNA (FIG. 5A). IκBα transcripts were considerably increased in cells infected with Ad-RORα1 (FIG. 5A). These findings indicate that RORα1 inhibits the NF-κB pathway by inducing the expression of the IκBα gene.

Figure 5B:
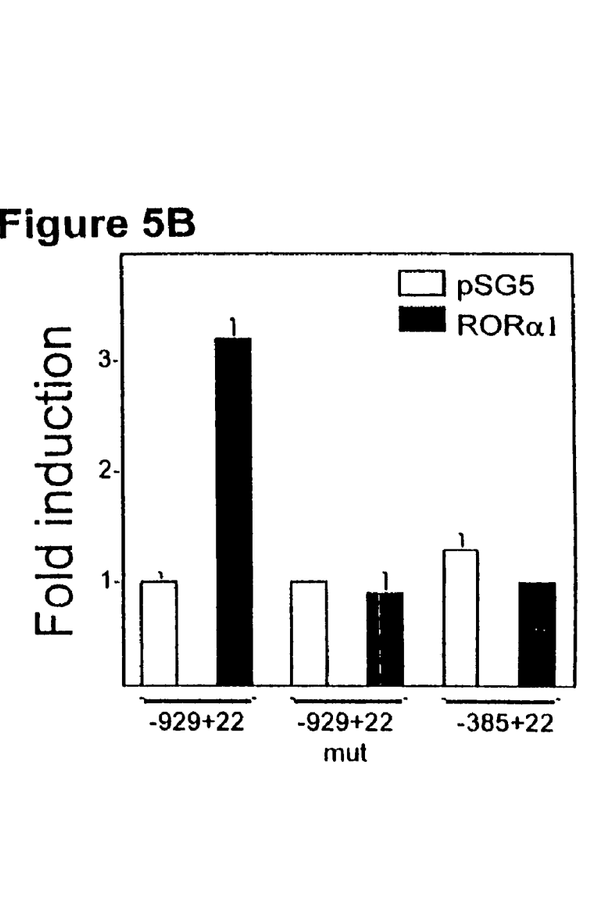

The fragment of the IκBα gene promoter between positions −929 and +22 was amplified by PCR and inserted upstream of the reporter gene luciferase (Ito, C. Y., Kazantsev, A. G. and Baldwin, A. S., Nucl. Acid Res. 1994, 22: 3787-3792). This construct forms the basis of the present invention. Cotransfection of this vector and an RORα1 expression vector induced an increase in luciferase activity under the control of the −929/+22 promoter but not the −385/+22 promoter. This indicates that the region regulated by RORα1 is located between positions −929 and −385 (FIG. 5B). Sequence analysis of this region revealed the presence of a response element (RORE) therein. Mutation of this RORE response element blocked the effect of RORα (FIG. 5B). This experiment unequivocally demonstrates the role of this site in RORα1-mediated induction of IκBα transcription.

Considering that the RORα gene has several isoforms (Giguère, V. et al., Genes & Dev. 1994, 8: 538-553), the inventors evaluated the effects of the isoforms RORα1, RORα2 and RORα3 on constructs under the control of two copies of the RORα response element present in the IκBα-RORE gene promoter cloned upstream of a heterologous promoter (TK promoter).

Figure 6A:
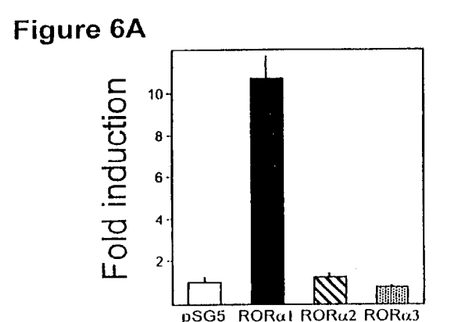
FIGS. 6A to 6C show the specific transcriptional activation of the IκBα gene by RORα1.

RORα1 strongly induced the activity of the reporter gene, which demonstrates that IκBα-RORE can function independently of the promoter. In contrast, RORα2 and RORα3 did not induce the transcription of the construct cited above (FIG. 6A), indicating that transcriptional activation of IκBα is specific of the RORα1 isoform.

Figure 6B:
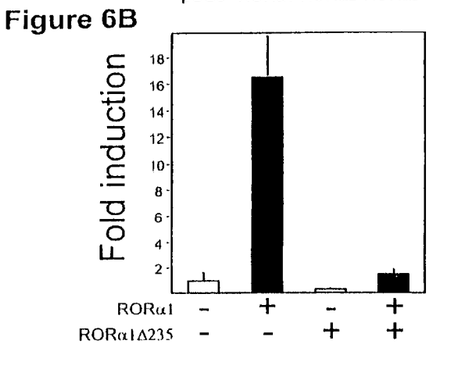
Figure 6C:
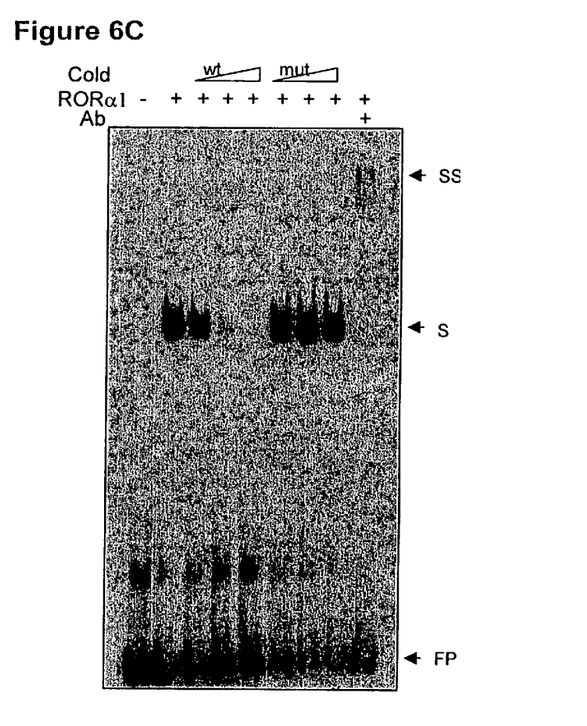

It has been shown that the negative dominant RORαΔ235 missing the LBD domain inhibits RORα1-induced transcription by competing with the same DNA binding domain (Mc Broom, L. D. B., Flock, G. and Giguère, V., Mol. Cell. Biol. 1995, 15: 796-808). The effect of this mutant on the promoter under the control of the IκBα gene RORE inducible by RORα1 was tested. Cotransfection with RORαΔ235 abolished the effect of RORα1 (FIG. 6B). This shows that binding of RORα to the promoter is essential for induction of transcription. Finally, binding of RORα1 to its response element RORE was checked by gel shift assays, using in vitro translated RORα1 protein. Competition experiments with unlabelled probes, native or mutated, or supershift experiments showed unequivocally that RORα1 binds with high affinity to the RORE site present in the IκBα gene promoter.

Thus, during the research conducted within the scope of the present invention, the inventors showed for the first time that overexpression of RORα1 in aorta smooth muscle cells inhibits the expression of COX-2, IL-6 and IL-8 induced by TNFα. All of these genes are major inflammatory markers in atherosclerotic lesions (Ross, R., New Engl. J. Med. 1999, 340: 115-126). The results that emerged from this research show that RORα exerts a protective role against atherosclerosis through a direct vascular effect in addition to its role as a modulator of lipoprotein metabolism (which occurs through its action on the expression of the apolipoprotein A1 gene (Mamontova, A. et al., Circulation 1998, 98: 2738-2743). By negatively regulating IL-8, a key chemokine closely involved in the recruitment of monocytes during the early stages of atherosclerosis (Ross, R., New Engl. J. Med. 1999, 340: 115-126), RORα1 can reduce the initiation and progression of atherosclerotic lesions.

The invention claimed is:

1. A vector comprising at least one copy of the Retinoid-related Orphan Receptor (ROR) response element site of the IKBα gene, operably linked to a minimal promoter wherein the minimal promoter is obtained from a promoter selected from the group consisting of the promoter of the herpes virus thymidine kinase (TK) gene, the cytomegalovirus (CMV) early promoter, the phosphoglycerate (PGK) promoter and the SV40 promoter, wherein said ROR response element site consists of SEQ ID NO: 1 or SEQ ID NO: 16, wherein SEQ ID NO: 16 is a mutated response element relative to the wild-type sequence SEQ ID NO: 1.

2. An isolated host cell comprising the vector according to claim 1.

3. A method of screening test substances to identify candidate substances useful for decreasing inflammation, wherein said method comprises the following steps: a) placing each test substance in contact with a nucleic acid construct containing at least one ROR response element site of the IKBα gene promoter, under conditions allowing each test substance to bind to said at least one response element site, b) identifying the test substances which effectively bind to the response element, c) selecting the test substances that bind to the response element as candidate substances useful for decreasing inflammation;

wherein said ROR response element site consists of SEQ ID NO: 1.

4. A method of screening test substances to identify candidate substances useful for decreasing inflammation, wherein said method comprises the following steps: a) placing each test substance in contact with a nucleic acid construct containing at least one ROR response element site of the IKBα gene promoter or a promoter containing said at least one ROR response element site wherein the nucleic acid construct is operably linked to a detectable nucleic acid under conditions allowing each test substance to bind to said at least one response element site, b) measuring expression of the operably linked nucleic acid to identify the test substances which effectively increase the transcriptional activity from the response element site or from the promoter; c) selecting the test substances that increase the transcriptional activity from the response element site or from the promoter as candidate substances useful for decreasing inflammation; wherein said ROR response element site consists of SEQ ID NO: 1.

5. The method according to claim 3 or 4, wherein in step a) the test substance is further placed into contact with a ROR and wherein step b) consists in measuring the possible binding of each test substance to the response element.

6. The method according to claim 5, wherein the measurement of step (b) is compared with a measurement carried out under conditions of step (a) and (b) but with a nucleic acid having the following sequence: GAGCACAATGTXXXXXXXGATAG (SEQ ID NO:16), wherein X is selected from the group consisting of A, T, C and G, wherein SEQ ID NO:16 is a mutated response element relative to the wild-type sequence SEQ ID NO:1.

7. The method according to claims 3 or 4, wherein the measurement of step (b) is compared with a measurement carried out under conditions of step (a) and (b) but with a nucleic acid construct having the following sequence: GAGCACAATGTXXXXXXXGATAG (SEQ ID NO:16), wherein X is selected from the group consisting of A, T, C and G, wherein SEQ ID NO:16 is a mutated response element relative to the wild-type sequence SEQ ID NO:1.

8. The method according to claim 4, wherein at step (a), the operably linked detectable nucleic acid is a reporter gene placed under the control of the promoter comprising said at least one ROR response element site of the IKBα gene promoter.

9. The method according to claim 8, wherein the reporter gene is selected from the group consisting of an IkBα gene, a chloramphenicol acetyltransferase gene, a firefly luciferase gene, a *Renilla* luciferase gene, a secreted alkaline phosphatase gene, and a beta-galactosidase gene.

10. The method according to claim 4, wherein at step (a), the operably linked nucleic acid is a reporter gene placed under the control the promoter comprising said at least one ROR response element site of the IKBα gene promoter, wherein said promoter comprising said at least one ROR response element site of the IKBα gene promoter is the promoter of an IKBα gene.

11. The method according to claim 10, wherein the reporter gene is selected from the group consisting of a IKBα gene, a chloramphenicol acetyltransferase gene, a firefly luciferase gene, a *Renilla* luciferase gene, a secreted alkaline phosphatase gene and a beta-galactosidase gene.

12. A method of screening test substances to identify candidate substances useful for treating inflammation, wherein said method comprises the following steps: a) placing each test substance in contact with a host cell transformed with a nucleic acid construct containing at least one reporter gene operably linked to a ROR response element site of the IKBα gene promoter or from a promoter containing said at least one ROR response element site, b) measuring the expression of the reporter gene by any suitable means and so identifying the test substances which effectively increase the transcriptional activity from the response element site or from the promoter containing said response element site and potentially bind to the response element, c) selecting the test substances that increase the transcriptional activity from the response element site or from the promoter containing said response element site as candidate substances useful for decreasing inflammation; wherein said Retinoid-related Orphan Receptor (ROR) response element site consists of SEQ ID NO:1.

13. The method according to claim 12, wherein the host cell of step (a) expresses a ROR.

14. The method according to claim 12, wherein the measurement of step (b) is compared with a measurement carried out under the same conditions as those of steps (a) and (b) but with a nucleic acid construct having the following sequence: GAGCACAATGTXXXXXXGATAG (SEQ ID NO:16), wherein X is selected from the group consisting of A, T, C, and G, wherein SEQ ID NO:16 is a mutated response element relative to the wild-type sequence SEQ ID NO:1.

* * * * *